(12) United States Patent
Edmiston et al.

(10) Patent No.: US 11,703,426 B2
(45) Date of Patent: Jul. 18, 2023

(54) PASSIVE SAMPLER

(71) Applicant: Arcadis U.S., Inc., Highlands Ranch, CO (US)

(72) Inventors: Paul Edmiston, Wooster, OH (US); Craig Divine, Dana Point, CA (US)

(73) Assignee: ARCADIS U.S., INC., Highlands Ranch, CO (US)

( * ) Notice: Subject to any disclaimer, the term of this patent is extended or adjusted under 35 U.S.C. 154(b) by 204 days.

(21) Appl. No.: 17/016,167

(22) Filed: Sep. 9, 2020

(65) Prior Publication Data

US 2021/0132024 A1    May 6, 2021

Related U.S. Application Data

(63) Continuation of application No. 16/926,144, filed on Jul. 10, 2020.

(60) Provisional application No. 62/928,799, filed on Oct. 31, 2019.

(51) Int. Cl.
| | | |
|---|---|---|
| *G01N 1/40* | (2006.01) |
| *G01N 1/22* | (2006.01) |
| *B01J 20/283* | (2006.01) |
| *G01N 1/10* | (2006.01) |
| *B01L 3/00* | (2006.01) |
| *G01N 33/18* | (2006.01) |

(52) U.S. Cl.
CPC .......... *G01N 1/2214* (2013.01); *B01J 20/283* (2013.01); *B01L 3/5023* (2013.01); *G01N 1/10* (2013.01); *G01N 1/405* (2013.01); *G01N 33/1826* (2013.01); *B01L 2200/10* (2013.01); *B01L 2300/069* (2013.01); *G01N 2001/2217* (2013.01)

(58) Field of Classification Search
CPC ................... G01N 1/2214; G01N 1/10; G01N 2001/2217; G01N 1/405; B01J 20/283; B01L 2200/10; B01L 2300/069
USPC .............. 73/862.25, 863.21, 863.23, 863.12; 422/535
See application file for complete search history.

(56) References Cited

U.S. PATENT DOCUMENTS 4,135,896 A * 1/1979 Parish ....................... G21F 9/02
96/417

FOREIGN PATENT DOCUMENTS

| CN | 102384895 | * | 3/2012 |
| KR | 1020150125841 | * | 11/2015 |

* cited by examiner

*Primary Examiner* — Robert R Raevis
(74) *Attorney, Agent, or Firm* — Howard M. Gitten, Esq.; Lewis Brisbois Bisgaard & Smith LLP (57) ABSTRACT

A passive sampling device is provided that is comprised of a member having a first surface and a second surface opposite the first surface and a hole through the member extending from the first surface to the second surface. An adsorbent material is positioned between two mesh members. The adsorbent material allows for efficient and selective removal of organic molecules, such as, for example, perfluoroalkyl substances.

11 Claims, 8 Drawing Sheets

PASSIVE SAMPLER

CROSS-REFERENCE TO RELATED APPLICATION

This application is a continuation of U.S. patent application Ser. No. 16/926,144 filed on Jul. 10, 2020 and claims priority to and the benefit under 35 U.S.C. § 119(e) to U.S. Provisional Patent Application Ser. No. 62/928,799 filed Oct. 31, 2019, both which are incorporated by reference in its entirety.

FIELD OF THE INVENTION

Embodiments of the present invention are generally related to devices for passively sampling groundwater and saturated soils.

BACKGROUND

The United States Environmental Protection Agency generally defines perfluoroalkyl substances (PFASs) as very stable manmade chemicals that have properties that allow them to repel both water and oil. PFASs are also heat resistant. The most commonly found and best-studied PFASs are perfluorooctanoic acid (PFOA) and perfluorooctanesulfonic acid (PFOS). The fat and water-repelling properties of PFASs allow them to be applied to almost any material to make it water, oil, and stain repellant. These properties were first used commercially in the 1950s in a variety of consumer products, including carpets, clothing, non-stick pans, paints, polishes, waxes, cleaning products, and food packaging. Firefighters and the military use PFASs in fire-suppressing foam. PFASs do not readily breakdown in the environment and are water-soluble. As a result, very low levels of PFASs exist in many areas of the environment and higher levels are found in water supplies near facilities that manufactured, disposed, or used PFASs. Accordingly, most individuals have been exposed to some form of PFASs in their life.

The development and demonstration of standardized procedures for field sampling of PFASs in environmental waters have been identified as a critical research priority (e.g., SERDP/ESTCP, 2017, Simon et al., 2019). Releases of PFASs are known or suspected at more than 300 Department of Defense (DoD) sites and, thus, the DoD's PFASs-related liabilities are expected to exceed $1 billion. The broader PFASs-related remediation and water treatment market is widely expected to reach $10 billion or more over the next decade (e.g., DoD, 2017; Environmental Business Journal, 2019).

Passive samplers are frequently used to measure water contaminants, such as chlorinated solvents (e.g., Vroblesky and Hyde, 1997), metals (e.g., Teasdale et al., 1995), and dissolved gases (e.g., Divine and McCray, 2004). Passive samplers are cost-effective, provide improved data quality, and greatly simplifying sampling methods. Because of their ubiquitous presence, PFASs sampling will greatly increase data quality and reliability of sampling results. Unfortunately, because of their ubiquitous presence in the environment and common materials and products, the risk for cross-contamination through conventional sampling methods is particularly high with PFAS (e.g., Denley et al., 2019). Because PFASs comprise a chemical class of more than 5,000 individual compounds, which represent unique and wide-ranging chemical characteristics, existing samplers and designs are not appropriate for many important PFASs constituents.

The most common passive samplers are based on a USGS U.S. Pat. No. 5,804,743 and are constructed of low-density polyethylene (LDPE) bags filled with deionized water. (See: https://www.itrcweb.org/Documents/PDBFAQs2.pdf & http://www.caslab.com/Passive-Diffusion-Bags-PDB-Samplers/). These existing designs are inadequate/inappropriate for PFASs compounds. More specifically, results from a Dixon-Anderson and Lohmann (2018) paper on passive samplers indicates LDPE is not an ideal semi-permeable membrane or adsorbent because concentration factors are relatively low and there is high variability (poor precision) in data obtained.

Battelle researchers, Kaltenberg and Pala (2018), reported preliminary testing results for several sorbents: specifically, graphite, LDPE, and two types of reticulated polyurethane foam (PUF)—ether and ester-based. In general, their results indicate PUF is not an ideal sorbent because PFASs sorption is highly nonlinear across the wide concentration range observed in environmental settings and is best described using a complicated Langmuir isotherm. This greatly increases the uncertainty when estimating the aqueous concertation in the tested waters.

Recently, Battelle announced its PFASs Insight™ Passive Sampler technology that reportedly consists of "a polymeric sorbent material suitable for neutral and ionic PFASs" (https://www.battelle.org/government-offerings/energy-environment/environmental-services/pfas-assessment-mitigation/passive-sampler-for-pfas). According to Battelle, "[l]aboratory testing has demonstrated relatively fast uptake of PFASs chemicals, with ≤1 week of equilibration times for most analyses." Reportedly, different geometries of the passive sampler hardware were designed to fit various application scenarios, including "groundwater monitoring wells and surface water."

The website presents laboratory data for some PFASs species but no further information on the sorbent material, sampler design, or experimental methods are provided. The website indicates there are plans for field testing of the device in the Summer of 2019.

Battelle researchers Kaltenberg et al. (2019) recently stated:
The research process involved preliminary trials to identify a suitable physical medium. Adsorption experiments were then conducted for 15 PFAS analytes ranging from anionic carboxylic acids and sulfonates of different chain lengths to PFAS precursors to determine their uptake kinetics and adsorption isotherms. The equilibrium between passive sampler and the sampled water was achieved in less than seven days for most of the analytes. The adsorption behaviour varied significantly between the analytes. The longer chain compounds demonstrated higher sorption than the shorter chains, and the sulfonates showed higher sorption compared to carboxylates. Sorption of PFAS onto the passive sampler was also affected by the water pH, ionic strength, and dissolved organic matter, which indicates the importance of considering these variables in PFAS site investigation and risk management planning.

However, the abstract does not identify sampler media.

Becanova et al. (2019) reported that they have tested and characterized two passive sampling approaches: i) a solid-phase microextraction (SPME) fiber sampler to determine PFASs in porewater; and ii) a microporous polyethylene (PE) tube sampler to assess PFASs in surface water. The polyacrylate (PA) SPME fibers were used to determine the equilibrium partitioning constant (KPA-W) and factors affecting the partitioning process. SPME fibers were exposed to 21 dissolved PFASs for various time periods (0 h to 48 h). After exposure, the PFASs concentration in water and fiber extracts were analyzed, and apparent equilibrium was reached within 24 hours. The partition coefficient increased with increasing length of the carbon chain and varied with PFASs functional group. They report some limited field results and note plans for further testing to evaluate the effects of water quality on sampler performance. The materials used in these samplers differ from the material used in one embodiment of the present invention described below. And it is not clear if this sampler is designed to monitor groundwater.

Thus, it is a long-felt need to provide a system and method that reliably facilitates passive PFASs sampling. Embodiments of the present invention provide a specialized and proprietary sorbent media in a tailored sampler design to maximize PFASs mass recovery and simplify sampling and analysis, resulting in improved PFASs measurement accuracy and precision at lower cost.

SUMMARY OF THE INVENTION

Accordingly, one object of the present disclosure is to provide a passive sampler that uses a unique polymeric organosilica sorbent. Polymeric adsorbents, which are generally defined as spherical synthetic polymers with defined pore structure and high surface area for efficient and selective removal of organic molecules, primarily in aqueous applications, have shown improved adsorption capacity for certain PFASs constituents (PFOA and PFOS, specifically) compared to activated carbon. In particular, hydrophobic organosilica media have been used to prepare granular adsorbents with high affinity and capacity for PFASs compounds.

The passive sampler design of some preferred embodiments of the present invention are based on the criterion that the devices need to be simple to deploy and analyzed with minimal training by field and laboratory technicians. In addition, the devices should be small enough to be placed inside small-diameter monitoring wells and various sampler housings (e.g., for surface water or stormwater collection). In one preferred embodiment, the samplers are transported and analyzed using polypropylene 30 mm by 15 mm centrifuge tubes. The samplers are constructed using only HDPE compatible with PFASs analysis. In these preferred embodiments, the analysis requires few manipulations, for example, little or no sampler disassembly. In these embodiments, all laboratory analyses are performed with standard existing equipment and consumables and the analytical method closely matches EPA 537.1 protocols. Moreover, the designs of the samplers in these embodiments are economical to reduce costs.

In one preferred embodiment, an equilibrium passive sampler is constructed using 250 mg of poly-QA-SOMS held in HDPE housing behind two windows of HDPE mesh. In this embodiment, the adsorbent is layered between two sides of mesh to allow direct flow through the granular poly-QA-Osorb and rapid transport. Using the open mesh design, the device can sample large volumes of water and come to equilibrium as quickly as possible.

In another preferred embodiment, a passive sampler is disclosed with a monolithic disk (e.g., 1 cm in diameter) of poly-QA-Osorb adsorbent mounted to HDPE. This embodiment is comprised of a unit of the same overall size but requires a longer equilibration time. In this embodiment, the disk faces the water on one side and, thus, allows for one-dimensional diffusion for simpler modeling. In these embodiments, the disk design allows for uniform manufacturing and constant sampler-to-sampler diffusion rates.

The present invention also discloses a method of sampling at least one type of PFAS that comprises a passive sampling device that is comprised of a member having a first surface and a second surface opposite the first surface, a hole through the member extending from the first surface to the second surface, a first mesh member interconnected to the first surface, a second mesh member interconnected to the second surface, and an adsorbent material positioned between the first mesh member and the second mesh member. In these preferred embodiments, a tether is added to the passive sampling device; the passive sampling device is deployed in a body of water or in saturated soil; the passive sampling device is recovered from the body of water or saturated soil; the passive sampling device is rinsed with water to remove debris; the passive sampler device is equilibrated in an aqueous solution with isotopically labeled surrogates, PFAS are extracted from the adsorbent material with methanol to desorb PFAS compounds, the extract is filtered through a SPE cartridge, the extract is dried, the dried extract is reconstituted in solvent, the PFAS compounds are analyzed.

The Summary is neither intended nor should it be construed as being representative of the full extent and scope of the present disclosure. The present disclosure is set forth in various levels of detail in the Summary, as well as in the attached drawings and the Detailed Description, and no limitation as to the scope of the present disclosure is intended by either the inclusion or non-inclusion of elements, components, etc. in this Summary. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. Further details and other features will become apparent after review of the following Detailed Description and accompanying drawing figures.

BRIEF DESCRIPTION OF THE DRAWINGS

Those of skill in the art will recognize that the following description is merely illustrative of the principles of the disclosure, which may be applied in various ways to provide many different alternative embodiments. This description is made for illustrating the general principles of the teachings of this disclosure invention and is not meant to limit the inventive concepts disclosed herein.

The accompanying drawings, which are incorporated in and constitute a part of the specification, illustrate embodiments of the disclosure and together with the general description of the disclosure given above and the detailed description of the drawings given below, serve to explain the principles of the disclosure.

In the Drawings.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

The present invention provides its benefits across a broad spectrum of endeavors. It is applicant's intent that this specification and the claims appended hereto be accorded a breadth in keeping with the scope and spirit of the invention being disclosed despite what might appear to be limiting language imposed by the requirements of referring to the specific examples disclosed. Thus, to acquaint persons skilled in the pertinent arts most closely related to the present invention, a preferred embodiment of the system is disclosed for the purpose of illustrating the nature of the invention. The exemplary method of installing, assembling and operating the system is described in detail according to the preferred embodiment, without attempting to describe all of the various forms and modifications in which the invention might be embodied. As such, the embodiments described herein are illustrative, and as will become apparent to those skilled in the art, can be modified in numerous ways within the scope and spirit of the invention, the invention being measured by the appended claims and not by the details of the specification.

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '______' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, subparagraph (f).

Figure 1:
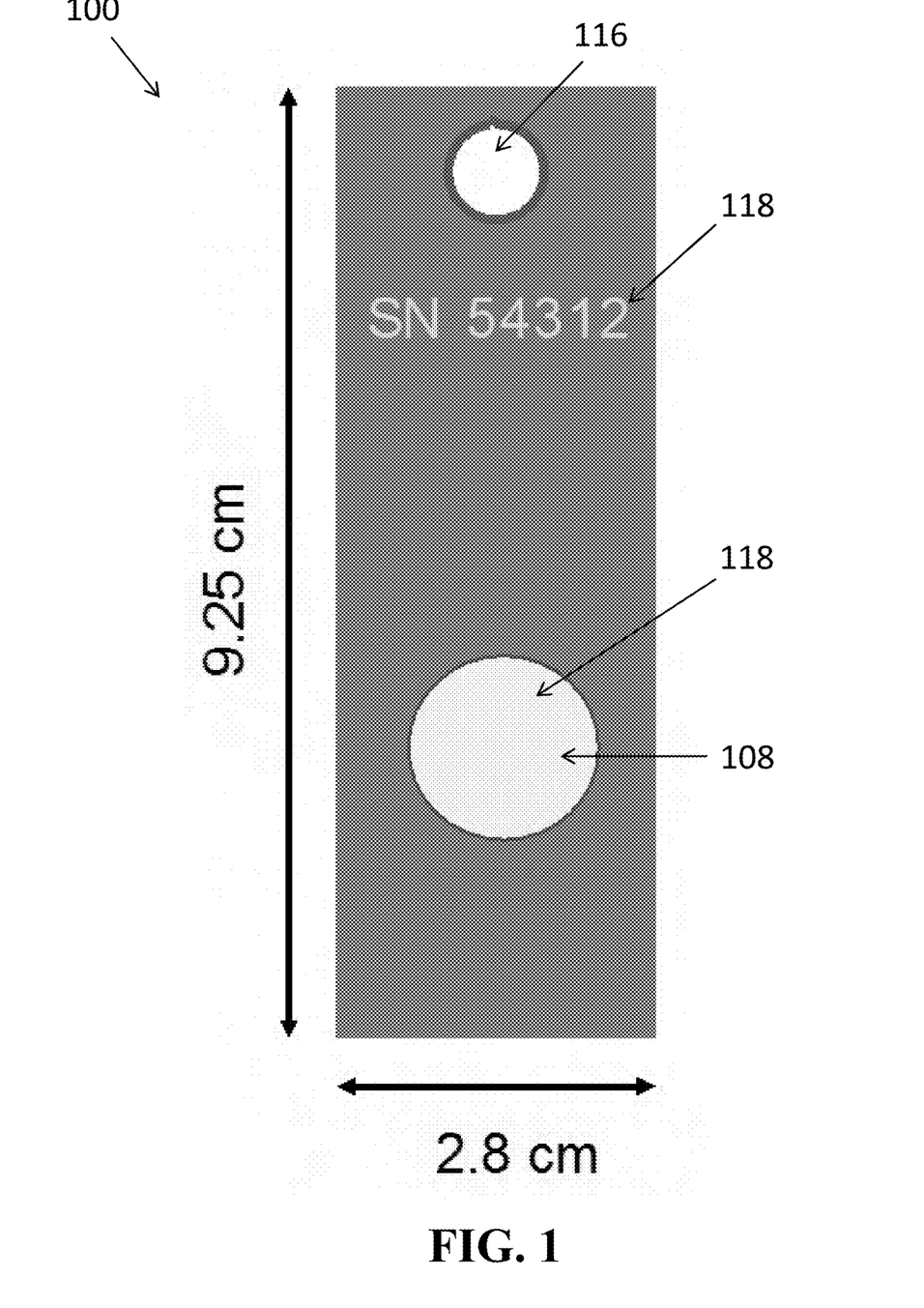
FIG. 1 is a front view of the system and assembly in to a preferred embodiment.
Figure 2:
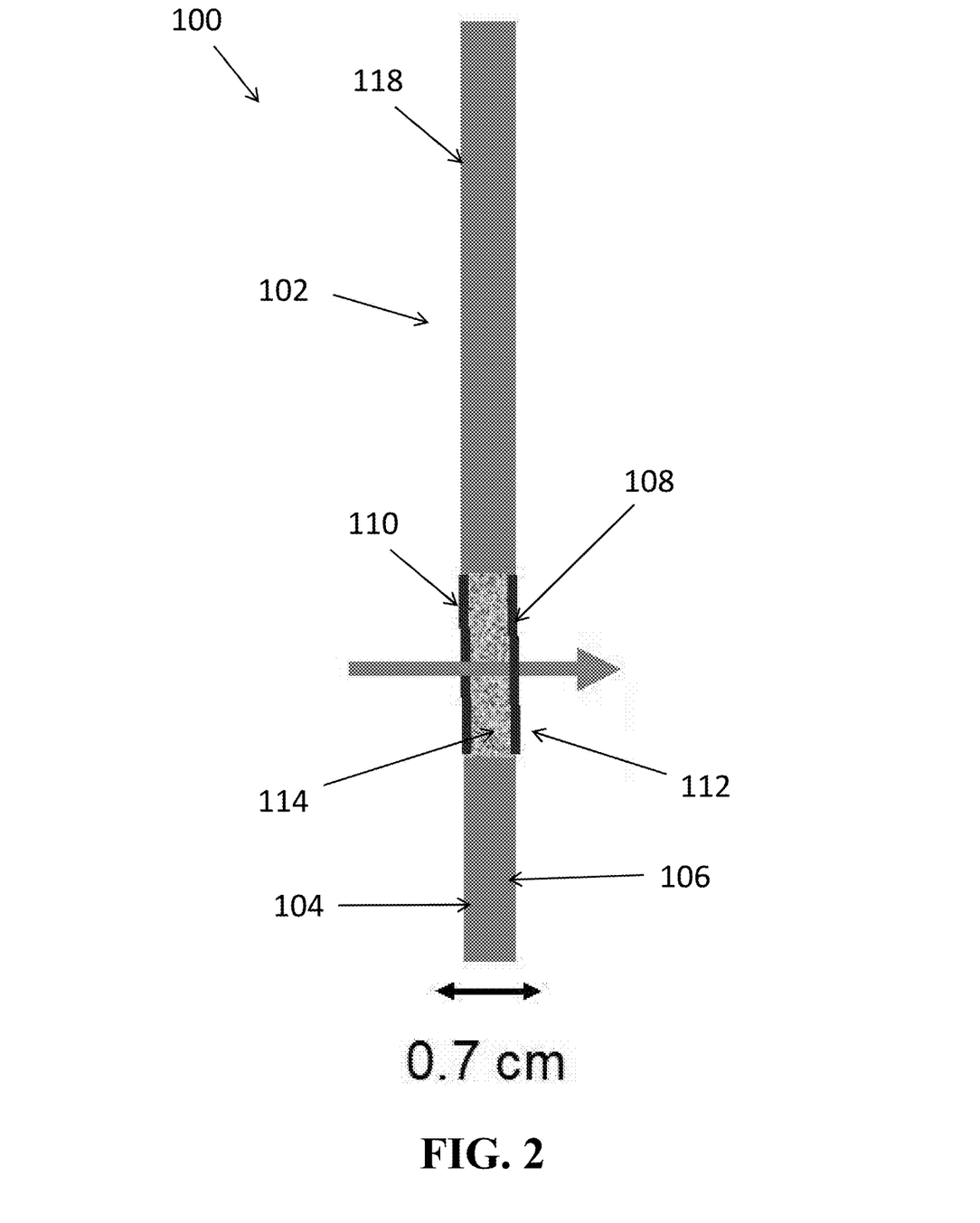
FIG. 2 is a perspective view of the system and assembly in to a preferred embodiment.

FIGS. 1 and 2 depict an embodiment of a passive sampling device 100, comprising a member 102 having a first surface 104 and a second surface 106 opposite the first surface 104 and a hole 108 through the member 102 extending from the first surface 104 to the second surface 106. In this embodiment, a first mesh member 110 is also disclosed, which is interconnected to the first surface 104. A second mesh member 112 is then interconnected to the second surface 106, and an adsorbent material 114 positioned between the first mesh member 110 and the second mesh member 112. The member 102 also comprises an attachment point 118, to which the member 102 can be mechanically coupled to another object or device. In this preferred embodiment, the member 102 is made of high-density polyethylene. In this preferred embodiment, the adsorbent material 114 is based on the use of a unique polymeric organosilica sorbent. The equilibrium passive sampler 100, as shown in FIGS. 1 and 2, comprises a member 102 constructed using 250 mg of poly-QA-SOMS held in high-density polyethylene housing behind two windows of high-density polyehylene mesh (mesh members 110 and 112) (see, FIGS. 1 and 2). In this embodiment, the adsorbent material 114 is layered between two sides of the mesh members 110 and 112 to allow direct flow through the granular poly-QA-Osorb and rapid transport. Using the open mesh design, the sampler 100 can sample large volumes of water and come to equilibrium as quickly as possible.

In these embodiments, the adsorbent material 114 comprises polymeric adsorbents, which are generally defined as spherical synthetic polymers with defined pore structure and high surface area for efficient and selective removal of organic molecules, primarily in aqueous applications. These adsorbent materials 114 have shown improved adsorption capacity for certain PFAS constituents (PFOA and PFQS, specifically) compared to activated carbon. In particular, hydrophobic organosilica media, which are commercially available as Osorb® sold by ABS Materials Inc., have been used to prepare granular adsorbents with high affinity and capacity for PFAS compounds.

Osorb® organosilica adsorbents are derived from the polycondensation of alkoxysilanes using a specific polymerization process to achieve molecular scale organization that imparts a high degree of mechanical flexibility (Burkett et al. 2008). Pores are hydrophobic, thus, the media adsorbs organic compounds from aqueous solutions without adsorbing water (Edmiston and Underwood 2009; Edmiston et al. 2016). A unique feature of Osorb® is that it can be synthesized with a flexible micropore structure allowing the material to expand more than 1.5 times in size when placed in solvents. This greatly increases the PFASs adsorptive capacity of the material. In the preferred embodiments described in FIGS. 1 and 2, the primary advantage of using a cationic polymer modified Osorb® (poly-QA-Osorb®) as the adsorbent material 114 is the ability to strongly adsorb PFAS compounds regardless of PFASs chain-length and charge-state. This means this adsorbent material 114 is applicable to compounds that range widely in carbon chain length, functional chemical groups, degree of fluorination, and isomerization. Furthermore, isotherms for many tested PFAS constituents are linear and predictable, particularly over the concentration range of primary interest and representative of common environmental conditions, making the contemplated material ideal for passive samplers, such as those disclosed in FIGS. 1 and 2.

Osorb® has previously been shown to work in passive samplers to monitor chlorinated compounds and munitions in sediment (Edmiston 2016). In those previous applications, Osorb® was encased in a stainless steel mesh inserted into sediments or placed in water. In third party testing, Osorb® was found to adsorb organic compounds well and had measured uptake rates better than or equal to Oasis HLB and Dowex Optipore™ L-493, especially in flowing water (Morrison and Beldon 2016).

In the preferred embodiments described in FIGS. 1 and 2, the adsorbent material 114 greatly concentrates PFASs constituents in a linear and predictable manner, allowing reliable measurement and quantitation in the tested water. This adsorbent material is unique and has not previously used for PFASs sampling. In these embodiments, equilibration times are short, i.e. less than about 2 days, and may be even shorter with slight modifications to the sampler geometry. Additionally, variations to the design decreasing equilibrations times will allow the sampler results to represent long time-average concentrations, which may be appropriate for certain applications (e.g., environmental risk assessments). In these preferred embodiments, the frame of the member 102 is small and therefore can be used in a wide range of applications. Retrieval lines and weights can be secured to the sampler, and the sampler can be readily secured to other protective housings or fixed features. In these embodiments, each sampler has a unique serial number 116 to minimize transcription and other errors. The serial number 116 may be encoded on a QR code that can support electronic data capture. The sampler 100 is also designed so that no sample preservation steps are required and minimal handling is necessary, reducing the potential for cross-contamination. Analysis of the sampler 100 is also straightforward and can be directly incorporated into existing commercial laboratory analytical procedures.

Figure 3:
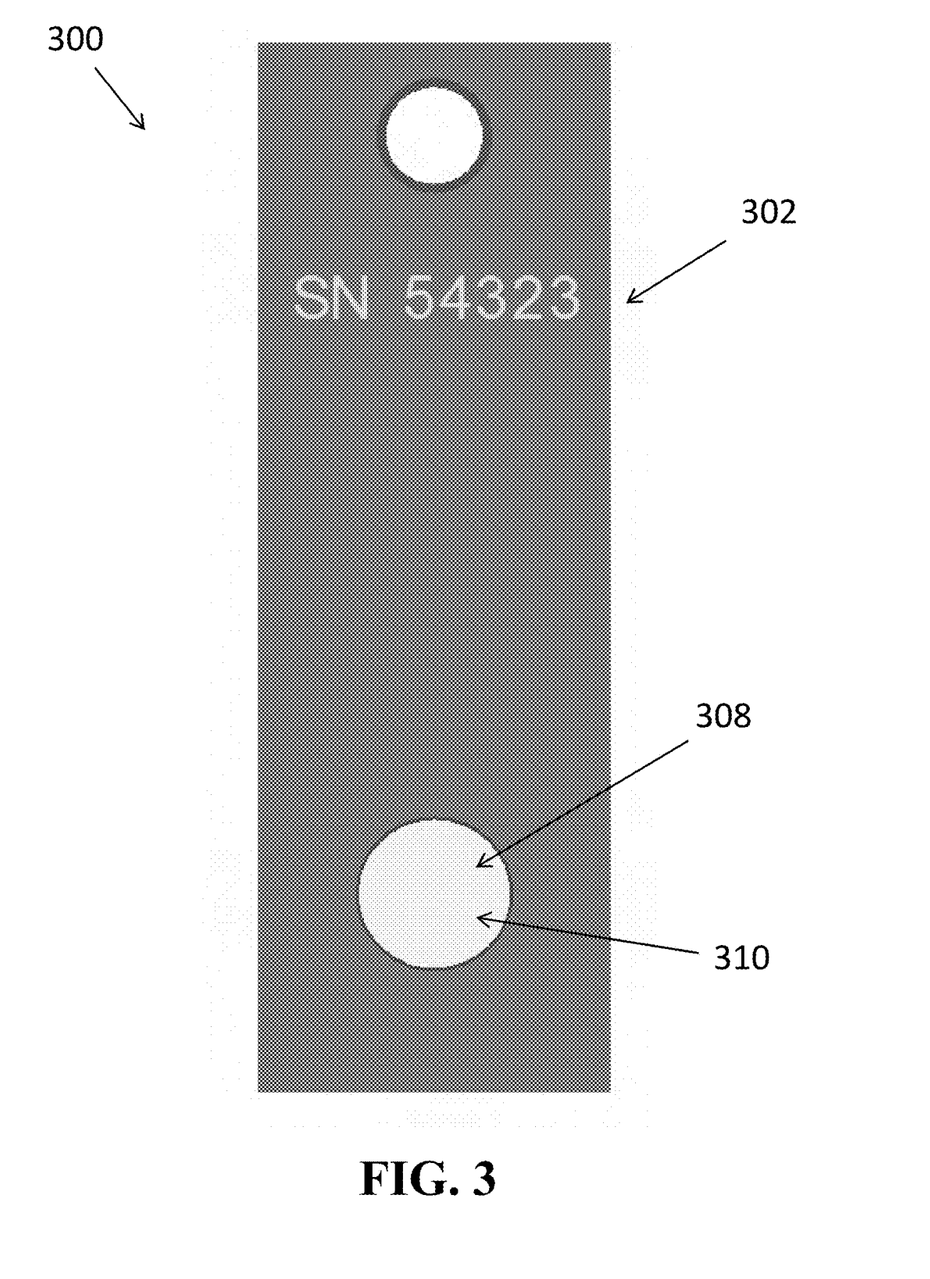
FIG. 3 is a front view of the system and assembly in to a preferred embodiment.
Figure 4:
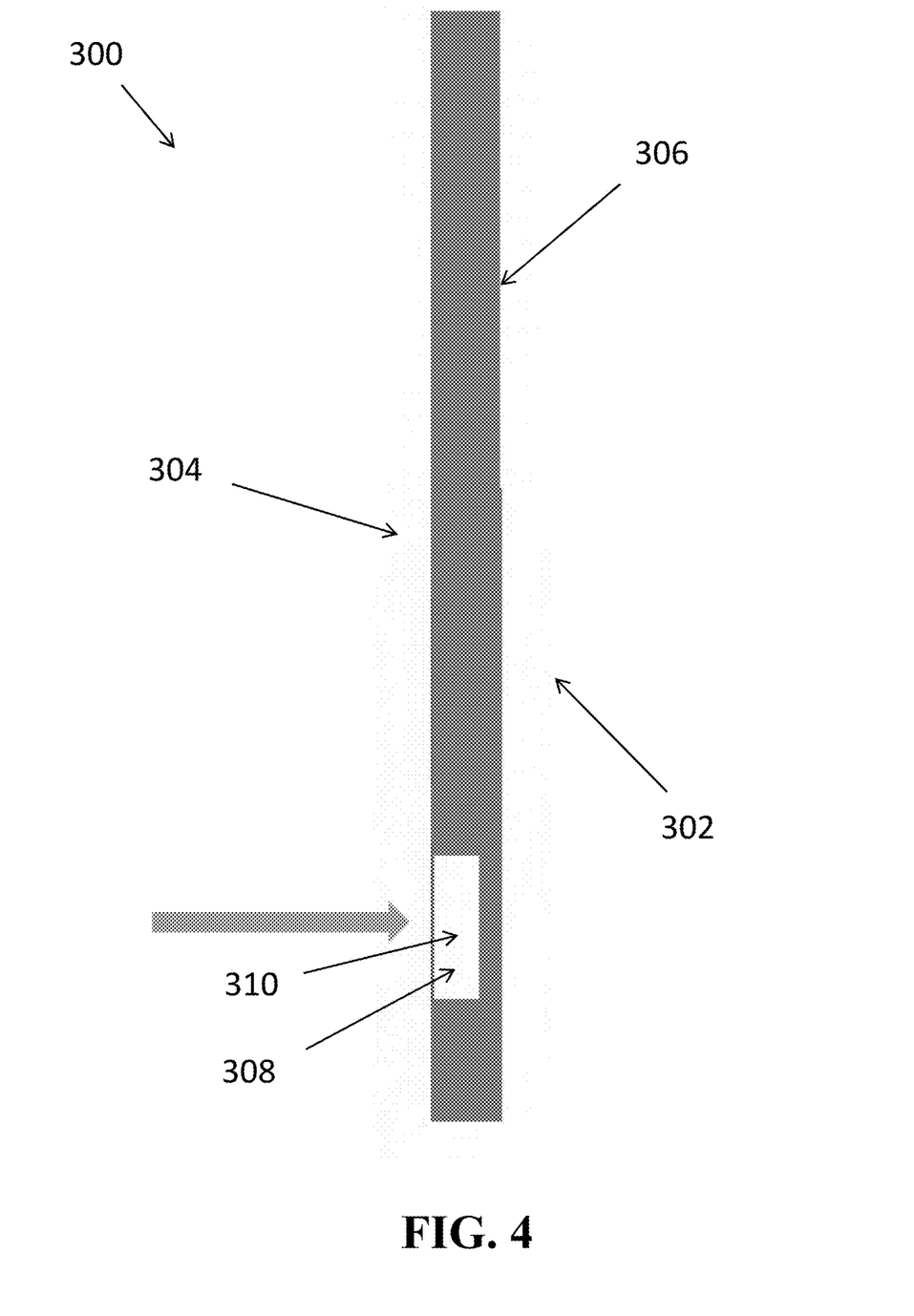
FIG. 4 is a perspective view of the system and assembly in to a preferred embodiment.

In another preferred embodiment, as shown in FIGS. 3 and 4, a passive sampling device 300 comprises a member 302 having a first surface 304 and a second surface 306 opposite the first surface 306, and a disc 308 of adsorbent material 310 interconnected to the first surface 304. In this preferred embodiment, the member 304 is made of high-density polyethylene and the disc 308 is porous. In this embodiment, the disc 308 of adsorbent material 310 is made up of hydrophobic organosilica media, such as, for example, Osorb®. The preferred embodiments shown in FIGS. 3-4 disclose a sampler 300 with a longer equilibration times, as compared the embodiments disclosed in FIGS. 1 and 2. In some preferred embodiments, the monolithic disk 308 is 1 cm in diameter of poly-QA-Osorb adsorbent mounted to HDPE, although various sizes may also be used depending upon application. The disk 308 faces the water on one side and, thus, allows for one-dimensional diffusion for simpler modeling. The disk design allows for uniform manufacturing and constant sampler-to-sampler diffusion rates.

The passive sampler designs described in FIGS. 1-4 are based on the criterion that the samplers need to be simple to deploy and analyzed with minimal training by field and laboratory technicians. In addition, the samplers should be small enough to be placed inside small-diameter monitoring wells and various sampler housings (e.g., for surface water or stormwater collection). For example, the member 102 disclosed in FIGS. 1 and 2, is 9.25 cm by 2.8 cm.

Accordingly, in some preferred embodiments the samplers must be transported and analyzed using polypropylene 30 mm by 15 mm centrifuge tubes. The samplers must be constructed using only HDPE compatible with PFASs analysis. The samplers must be able to be analyzed without many manipulations and little or no sampler disassembly. All laboratory analyses must be performed with standard existing equipment and consumables and the analytical method should closely match EPA 537.1 protocols. The design in most preferred embodiments also should be economical to reduce costs.

Results from laboratory equilibration experiments confirm the Osorb® performance and the sampler design. The testing was done by soaking a passive sampler, like the one described in FIGS. 1 and 2, in a 1L bottle of PFASs (2.0 ppm each). The solution was very slowly stirred and small aliquots of the water were sampled and tested for residual PFASs concentration. The equilibrium time is about 7 days (faster for some constituents) with apparent distribution coefficients (Kd) of about 10,000.

In the preferred embodiment used in the testing described above, the contemplated Osorb-based passive sampler is an all HDPE plastic device that is approximately 25 mm in width where the sorbent (granular) is held between mesh screens. The Osorb® media is between about 4 mm thick and about 15 mm in diameter and is exposed to the water to be sampled on two sides. Sampler equilibration time is governed by the effective solute diffusion coefficient in the Osorb matrix. Based on typical open water diffusion coefficients (D; $>10e^{-5}$ cm$^2$/sec) and diffusion coefficients in LDPE measured for a variety of solutes by Divine and McCray (2004; $>10e^{-7}$ cm$^2$/sec), it is expected that diffusion coefficients for granular Osorb® will likely be between about $1 \times 10e^{-8}$ cm$^2$/sec and $1 \times 10e^{-7}$ cm$^2$/sec. The simple geometry allows the sampler to be considered as plane sheet with zero concentration initially and the boundary conditions on the two surfaces at a constant concentration. Therefore, the predicted concentration within sampler at various times and distances from the sampler boundary is given by the solutions in Hwang and Huang (2012) and is compared to preliminary laboratory data.

Figure 9:
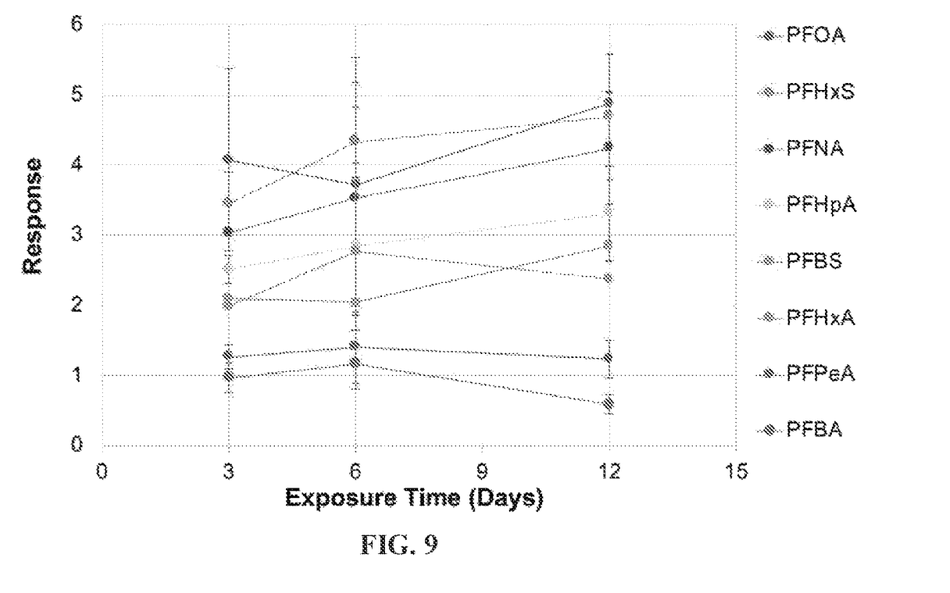
FIG. 9 is a table showing Passive Sampler Response Data-2 ppb PFAs, simulated groundwater 5.5 cm cm/hr flow rate (slow near quiescent).
Figure 10:
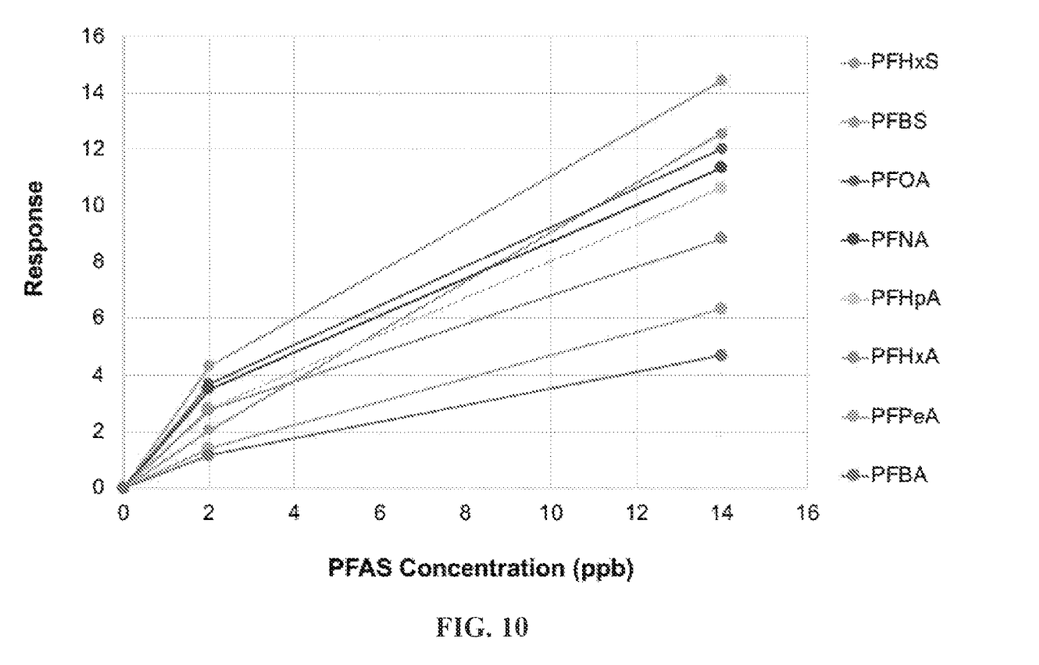
FIG. 10 is a table showing Passive Sampler Response vs. Concentration Data-simulated groundwater, 5.5 cm/hr flow rate (slow near quiescent), 6 day equilibrium time.

Experimental results that show the sampler equilibrates rapidly at different concentrations for several PFASs. In the embodiments shown in FIGS. 9 and 10, the samplers were placed in very slowly moving simulated groundwater for a period of time, removed, and soaked in isotopically labeled surrogate solution. The PFASs were desorbed and then analyzed. The response (y-axis in the graphs) is defined as the peak area of analyte divided by the peak area of the surrogate.

Based on the design criteria and overall method of analysis surrogates and internal standards can be incorporated to mimic EPA 537.1 and existing QSM 5.2 DoD PFAS analytical methods.

Figure 5:
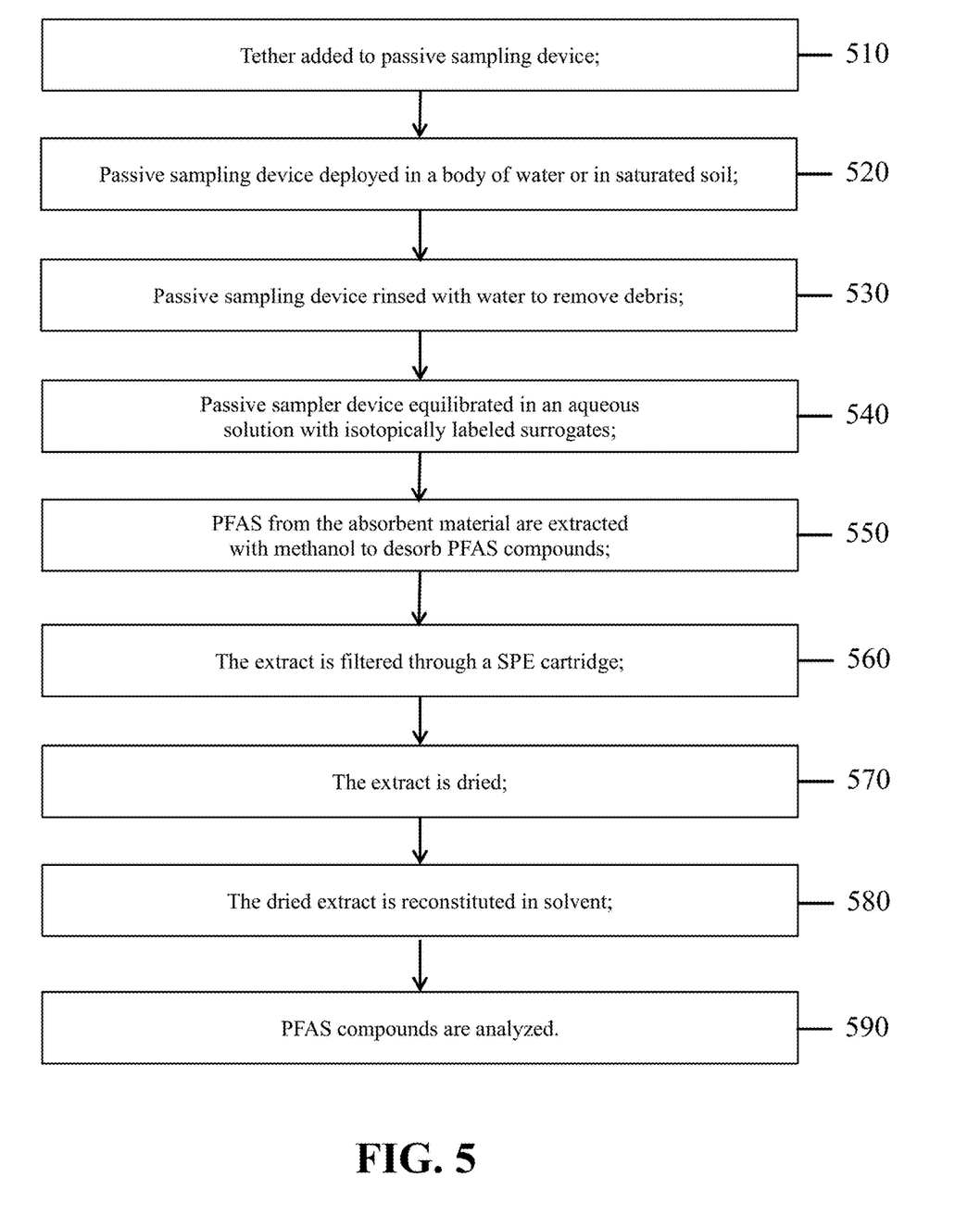
FIG. 5 shows the steps of a method of passive sampling according to embodiments of the present disclosure.
Figure 6:
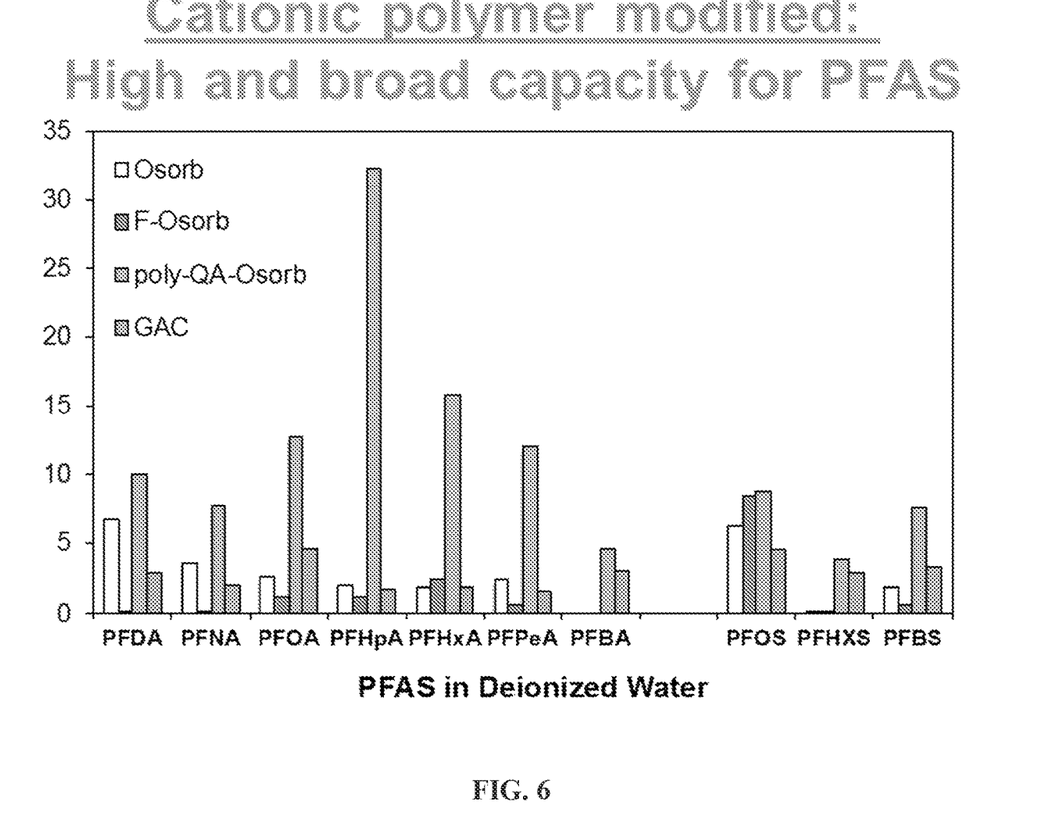
FIG. 6 is a table showing the affinity of selected materials for PFAS compounds.
Figure 7A:
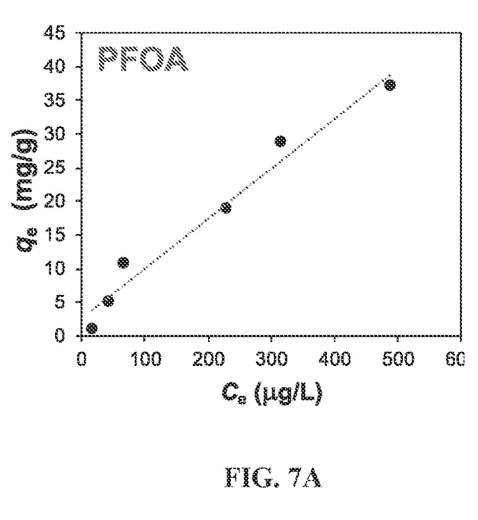
FIGS. 7A and 7B show linear adsorption isotherms for PFOA and PFOS in deionized water for poly-AQ-Osorb.
Figure 7B:
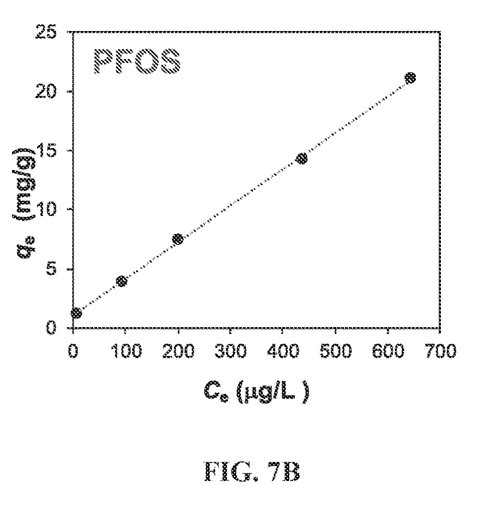
Figure 8:
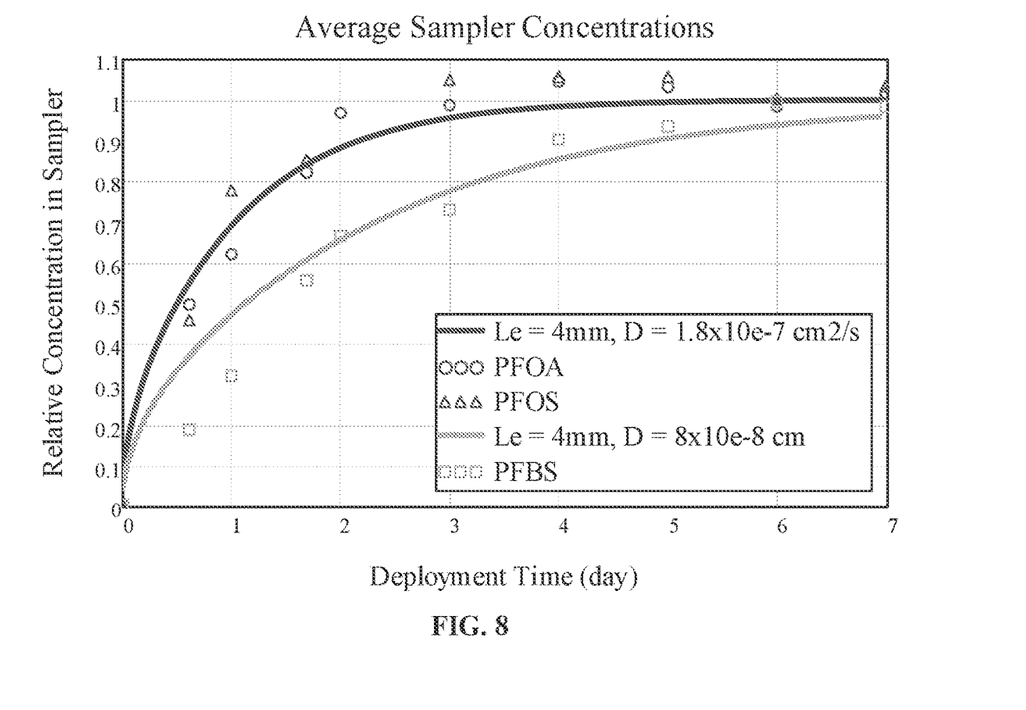
FIG. 8 is a table showing a comparison of predicted to actual passive sampler equilibration for three PFAS constituents.

The present invention also discloses a method of sampling at least one type PFAS, in which a tether is added to the passive sampling device 510; the passive sampling device is deployed in a body of water or in saturated soil 512; the passive sampling device is recovered from the body of water or saturated soil 514; the passive sampling device is rinsed with water to remove debris 516; the passive sampler device is equilibrated in an aqueous solution with isotopically labeled surrogates 518; PFAS are extracted from the adsorbent material with a solvent to desorb PFAS compounds 520; the extract is filtered 522; the extract is dried 524; the dried extract is reconstructed in solvent 526; the PFAS compounds are analyzed 528. In some preferred methods, the sampler is soaked in surrogates after deployment. In these embodiments, <2 mL of methanol (or other solvent) can be applied to the contained sorbent and then the entire sampler can be spun in a centrifuge tube to "spin out" the methanol. In some preferred embodiments, the extract is filtered through a SPE cartridge.

The present invention also discloses a system and method for at home sampling. In these preferred embodiments, an individual can purchase an at home virgin sampler to sample, for example, tap water at the individual's residence or business. In these embodiments, the sampler would be placed in a common drinking glass, which is then filled with tap water and placed under a dripping tap in the sink overnight. The constant low flow of water maintains a steady concentration at the sampler boundary, enabling equilibration with the average concentration in the water over the sampling period. In other preferred embodiments, the sampler is placed in a specified-volume container, which is provided with the sampler. In these embodiments, the container is filled and the sampler would be allowed to equilibrate for a specified period of time. In both of these preferred embodiments, the individual user can send the sampler to a lab via a FedEx mailing envelope or similar, without the need for special equipment or shipping water.

The above-described benefits, embodiments, and/or characterizations are not necessarily complete or exhaustive, and in particular, as to the patentable subject matter disclosed herein. Other benefits, embodiments, and/or characterizations of the present invention are possible utilizing, alone or in combination, as set forth above and/or described in the accompanying figures and/or in the description herein below.

The phrases "at least one," "one or more," and "and/or," as used herein, are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

Unless otherwise indicated, all numbers expressing quantities, dimensions, conditions, and so forth used in the specification and drawing figures are to be understood as being approximations which may be modified in all instances as required for a particular application of the novel assembly and method described herein.

The term "a" or "an" entity, as used herein, refers to one or more of that entity. As such, the terms "a" (or "an"), "one or more" and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials, or acts and the equivalents thereof shall include all those described in the Summary, Brief Description of the Drawings, Detailed Description and in the appended drawing figures.

What is claimed is:

1. A method of at home sampling comprising:
providing a passive sampling device to a user, comprised of
a member having a first surface and a second surface opposite the first surface;
a hole through the member extending from the first surface to the second surface;
a first mesh member interconnected to the first surface;
a second mesh member interconnected to the second surface; and
an adsorbent material positioned between the first mesh member and the second mesh member;
placing the passive sampling device in a drinking glass;
placing the passive sampling device under a tap water faucet in the user's home;
filling the drinking glass with tap water;
leaving the tap water faucet on to continuously drip into the drinking glass, wherein the tap water faucet maintains a constant low flow of tap water into the drinking glass for a sampling period, and wherein the drinking glass is constantly overflowing thus creating a continuous flow-through cell; and
enabling equilibration of the passive sampling device in the tap water over the sampling period.

2. The method of claim 1, wherein the sampling period is between 12 and hours from when the passive sampling device is first placed into the tap water.

3. The method of claim 1, wherein the sampling device samples at least one type of perfluoroalkyl substance.

4. The method of claim 1, wherein the member is made of high-density polyethylene.

5. The method of claim 1, wherein the member forms a high-density polyethylene housing, the first mesh member forming a first window, the second mesh member forming a second window, each mesh member being formed of high-density polyethylene mesh, and between 100 and 500 mg of organosilica adsorbent being disposed between the first mesh window and second mesh window.

6. The method of claim 5, wherein the organosilica adsorbent is synthesized with a flexible micropore structure allowing the media to expand more than 1.5 times in size after being exposed to at least one type of perfluoroalkyl substance when placed in a solvent.

7. The method of claim 1, wherein the adsorbent material concentrates at least one type of perfluoroalkyl substance in a predictable manner, which allows for reliable measurement and quantitation of the at least on type of perfluoroalkyl substance in the tested solvent.

8. The method of claim 1, wherein the adsorbent material adsorbs at least one type of perfluoroalkyl substance regardless of the perfluoroalkyl substance chain-length and charge-state.

9. The method of claim 1, wherein the adsorbent material adsorbs compounds that range in carbon chain length, functional chemical groups, degree of fluorination, and isomerization.

10. The method of claim 1, wherein the member further comprises a unique serial number, wherein the serial number minimizes transcription errors.

11. The method of claim 10, wherein the serial number is encoded on a QR code that supports electronic data capture.

\* \* \* \* \*